United States Patent [19]

Tomita et al.

[11] Patent Number: 5,360,546
[45] Date of Patent: Nov. 1, 1994

[54] METHOD FOR TREATING ORGANIC SLUDGE

[75] Inventors: Yoshiho Tomita, Kasugai; Noriaki Inagaki, Handa; Atsushi Miyata, Handa; Shigehiro Suzuki, Handa, all of Japan

[73] Assignee: NGK Insulators, Ltd., Japan

[21] Appl. No.: 40,609

[22] Filed: Mar. 31, 1993

[30] Foreign Application Priority Data

| | | | |
|---|---|---|---|
| Apr. 1, 1992 | [JP] | Japan | 4-079905 |
| Jun. 18, 1992 | [JP] | Japan | 4-159258 |
| Aug. 14, 1992 | [JP] | Japan | 4-216922 |
| Sep. 22, 1992 | [JP] | Japan | 4-252879 |
| Feb. 8, 1993 | [JP] | Japan | 5-020160 |

[51] Int. Cl.$^5$ .............................................. C02F 11/04
[52] U.S. Cl. ................................. 210/603; 210/609; 210/613; 210/631
[58] Field of Search .............. 210/603, 608, 609, 613, 210/624, 625, 631

[56] References Cited

U.S. PATENT DOCUMENTS

| | | | |
|---|---|---|---|
| 3,622,507 | 11/1971 | Pasveer | 210/631 |
| 4,022,665 | 5/1977 | Ghosh | 210/603 |
| 4,119,495 | 10/1978 | Belyaev et al. | 210/631 |
| 4,213,857 | 7/1980 | Ishida et al. | 210/631 |
| 4,240,904 | 12/1980 | Dassen | 210/613 |
| 5,015,384 | 5/1991 | Burke | 210/603 |

FOREIGN PATENT DOCUMENTS

| | | |
|---|---|---|
| 0220647 | 5/1987 | European Pat. Off. . |
| 391976 | 3/1990 | Germany . |
| 3833039 | 4/1990 | Germany . |
| 4-326998 | 11/1992 | Japan . |
| 8804282 | 6/1988 | WIPO . |

OTHER PUBLICATIONS

Korrespondenz Abwasser. vol. 36, No. 1, Jan. 1989, Augustine De, pp. 84–95.

Patent Abstracts of Japan, vol. 5, No. 160 (C-075) 15 Oct. 1981 & JP-A-56 091 898 (Nishihara Environ Sanit Res) 25 Jul. 1981.

Database WPIL, Section Ch, Week 4182, Derwent Publications Ltd., London, GB; Class D15, An 82-87030E & JP-A-57 144 099 (Hitachi Plant Eng Const) 6 Sep. 1982.

R. V. Rajan et al., "Low-Level Chemical Pretreatment for Enhanced Sludge Solubilization", Nov./Dec. 1989, pp. 1678–1683.

Yu-You Li et al., "Upgrading of Anaerobic Digestion of Waste Activated Sludge by Thermal Pretreatment", May, 1992.

*Primary Examiner*—Christopher Upton
*Attorney, Agent, or Firm*—Parkhurst, Wendel & Rossi

[57] ABSTRACT

A method for treating an organic sludge is provided which can sufficiently and efficiently solubilize an organic sludge to afford a high load of anaerobic digestion treatment with an improved digestion ratio and methane gas recovery amount thereby to widely decrease the amount of the organic sludge discharged from the method. The method includes a hot alkaline treatment for causing the organic sludge to become alkaline while maintaining the temperature of the sludge to ambient $-100°$ C. to solubilize organic matters in the sludge, and an anaerobic digestion treatment of anaerobically digesting the organic sludge after the hot alkaline treatment at a temperature of 20°–60° C. at a pH of 7.3–9.2.

17 Claims, 10 Drawing Sheets

FIG_3

FIG_4

FIG_7

METHOD FOR TREATING ORGANIC SLUDGE

BACKGROUND OF THE INVENTION

1. Field of the Invention

The present invention relates to a method for treating organic sludges, particularly for treating organic sludges, such as, sewage sludge, etc., including the steps of solubilizing the sludge, and then digesting the solubilized sludge in an anaerobic condition.

2. Related Art Statement

Recently, treatment and disposal of organic sludges produced in large amounts in sewage-treating plants has become a serious social problem. Anaerobic digestion of an organic sludge improves treatability of the sludge to improve stability, innoxiousness, volume reduction, and dehydration property, etc., of the sludge when used as a reclaiming substance, and recovery of methane gas as a valuable resource from the sludge. The recovering of methane gas as a valuable resource has been adopted in sewage-treating plants and the like as a useful method for treating organic sludges because of increased amounts of recovered methane due to qualitational change of organic components of organic sludges resulting from the consumers' life of the current society and because of development of a technique for generating electric power from the recovered methane gas, and many sewage-treating plants have been operated using one phase reaction type reaction tank at a medium digestion temperature of about 37° C. However, at present, such method are still low in digestion ratio and insufficient in volume reduction and methane gas recovery and reduction of organic matter concentration. Therefore, in order to solve such problems many methods have been researched and studied of heating a sludge (heating method) to accelerate solubilization of the sludge at a prestige of the anaerobic digestion and thereafter treating the solubilized sludge in an anaerobic condition. These methods are summarized as follows.

In these methods, an organic sludge is agitated under heating at around 60° C. in a heating tank, and then anaerobically treated in an anaerobic digestion tank. If the methods are applied to an organic sludge like a sewage sludge resulting from microorganisms, a low solubility value of 10–30% is merely obtained which is not worth the thermal energy applied for heating, so that a low digestion ratio of 50% at the most can merely be obtained, and hence predominance of the anaerobic treatment of organic sludges is not yet settled. Moreover, the digestion gases obtained by the above conventional methods have low methane contents, so that they could not increase electric power generation efficiency of electric fuels or the like when supplied thereto as a raw material gas for electric power generation.

Furthermore, in separating solids from liquid phase of a digested sludge, conventionally a gravitational concentration method has been mainly used. However, such a gravitational concentration method can not sufficiently separate solids from liquid phase of a digested sludge, so that they have problems as follows.

1 Concentration of the concentrated digested sludge is so low that the abilities for the subsequent dehydration process and drying process are deteriorated.

2 Solids and the like are existing in intermingled state in the liquid phase of the digested eluate, so that the load of a subsequent water treating system is increased if the digested eluate is directly returned as a return water to the water treating system.

3 In the anaerobitic digestion process, phosphorus of ortho phosphorus state is dissolved out from the solubilized and digested sludge, so that the concentration of phosphorus of ortho phosphorus state in the digested eluate is high.

Another problem of the gravitational concentration method is that the separation speed of the method separating the solids from the liquid phase of digested sludge is so low that the capacity of the solid/liquid separation tank must be equally large to that of the anaerobic digestion tank.

Meanwhile, a solid/liquid separation method which obviates the problems of the gravitational concentration method has been known which is a so-called "pressurized floating concentration method". This is a solid/liquid separation method mainly used in a process of concentrating a sludge and utilizes a phenomenon that a sludge is floated when a pressure is exerted on the sludge to dissolve a gas, such as, air into the sludge and then liberated to adhere the gas of a foamed state to the sludge. However, this method has a problem of necessitating a large amount of electric power for exerting a high pressure to the sludge and complicated equipment for practicing the method.

Also, an anaerobic digestion method has been known wherein a hot alkaline treating tank of accelerating the solubilization of an organic sludge by adding an alkaline to the sludge while heating the sludge is provided at a prestige of the anaerobic digestion tank which performs anaerobic digestion at a medium temperature of about 37° C. during the anaerobic digestion treatment. This method has advantages that the digestion ratio is high and the amount of recovered methane is large. In this way, an organic sludge after the hot alkaline treatment and the anaerobic digestion treatment is subjected to the solid/liquid separation treatment at where it is separated to a concentrated sludge and a digested eluate, and the digested eluate is directly returned to a subsequent water treatment system. However, this method has a problem of containing a large amount of phosphorus and nitrogen in the digested eluate, so that the load of the water treatment system is largely increased.

SUMMARY OF THE INVENTION

An object of the present invention is to obviate the above problems.

Another object of the present invention is to accelerate solubilization rate of an organic sludge at the anaerobic digestion stage and to accelerate acidic fermentation and methane fermentation to improve digestion ratio thereby to increase the amount of recovered methane.

A further object of the present invention is to effectively utilize the generated methane as a raw material gas for fuel cells and the like for generating electric power.

A still further object of the present invention is to provide a solid/liquid separation method for a digested sludge which can separate digested solids from digested liquid phase of the digested sludge at a sufficiently high rate. Herein, the word "digested solids" means the concentrated solids of digested sludge, and the word "digested liquid" means digested eluate. Another object of the present invention is to provide a method of treating a digested eluate to remove phosphorus and nitrogen from the digested eluate and to recover valuable ammonium magnesium phosphate hexahydrate.

A further object of the present invention is to solubilize sewage and the like organic sludge by an alkaline treatment and then anaerobically digest the solubilized organic sludge.

Now, the above objects can be achieved by the present invention.

The present invention is a method for treating an organic sludge, comprising a hot alkaline treatment of causing the organic sludge to an alkaline condition while maintaining the temperature of the sludge to ambient −100° C. to solubilize organic matters in the sludge, and an anaerobic digestion treatment of anaerobically digesting the organic sludge after the hot alkaline treatment at a temperature of 20°-60° C. at a pH of 7.3-9.2. This method will sometimes be called as "first method of the present invention" hereinafter.

The present invention is also a method for treating an organic sludge, comprising a hot alkaline treatment of causing the organic sludge to an alkaline condition while maintaining the temperature of the sludge to ambient −100° C. to solubilize organic matters in the sludge, and an anaerobic digestion treatment of anaerobically digesting the liquid of the hot alkaline treated organic sludge separated from the solids of the hot alkaline treated organic sludge after the hot alkaline treatment at a temperature of 20°-60° C. at a pH of 7.3-9.2. This method will sometimes be called as "second method of the present invention" hereinafter.

The present invention is also a method for treating an organic sludge, wherein a digested gas obtained from either of the first and second methods of the present invention is used as a raw material gas for generating electric power and/or thermal energy therefrom. This method will sometimes be called as "third method of the present invention" hereinafter.

The present invention is also a method for treating a digested sludge, comprising lowering the pH of the digested sludge having an increased total amount of concentrations of carbonate ions, bicarbonate ions and dissolved carbon dioxide obtained by the anaerobic digestion treatment according to the first present method of anaerobically digesting an organic sludge after the hot alkaline treatment at a temperature of 20°-60° C. at a pH of 7.3-9.2 to liberate gaseous carbon dioxide from the digested sludge, and utilizing the liberated gas for floating the digested sludge in the digested eluate to separate the digested solids from the digested eluate, while adding a flocculent to the digested solids to dehydrate the digested solids. This method will sometimes be called as "fourth method of the present invention" hereinafter.

The present invention is also a method for treating an organic sludge, comprising adding to a digested sludge obtained by the anaerobic digestion treatment according to the first method of the present invention, or to a digested eluate obtained by liquid/solid separation of the digested sludge, or to a digested eluate obtained by anaerobically digestion treating the alkaline treated liquid of the second method of the present invention at least one or two of $Mg^{2+}$, $NH_4^+$ and $PO_4^{3-}$, depending upon the components desired to be removed to crystallize ammonium magnesium phosphate hexahydrate, separating the crystallized ammonium magnesium phosphate hexahydrate from the liquid phase of the digested sludge or the digested eluate thereby to recover ammonium magnesium phosphate hexahydrate and remove phosphorus and/or nitrogen from the digested sludge or the digested eluate. This method will sometimes be called as "fifth method of the present invention" hereinafter.

Usually, the methods of the present invention are illustrated by the flow sheet as shown in FIG. 8.

The present invention is also a method for treating an organic sludge by anaerobic digestion, comprising subjecting an incoming sewage containing organic sludge to a solids/liquid precipitation treatment in an initial precipitation pond to obtain an initially precipitated sludge and an initially separated liquid, subjecting the initially precipitated sludge to a hot alkaline treatment at a temperature of abmient-anaerobical digestion temperature, preferably 20°-60° C., to solubilize the initially precipitated sludge, aerating the initially separated liquid in an aeration apparatus, subjecting the aerated initially separated liquid to a solids/liquid separation treatment in a solids/liquid separation apparatus to obtain an excessive sludge, subjecting the excessive sludge to a hot alkaline treatment at a temperature of 50°-100° C., preferably 50°-70° C., to solubilize the excessive sludge, mixing the solubilized initially precipitated sludge and the solubilized excessive sludge to obtain a mixed sludge, and anaerobically digesting the mixed sludge. This method will sometimes be called as "sixth method of the present invention", hereinafter.

BRIEF DESCRIPTION OF THE DRAWINGS

For a better understanding of the present invention, reference is made to the accompanying drawings, in which.

Numbering in the drawings.

Figure 1:
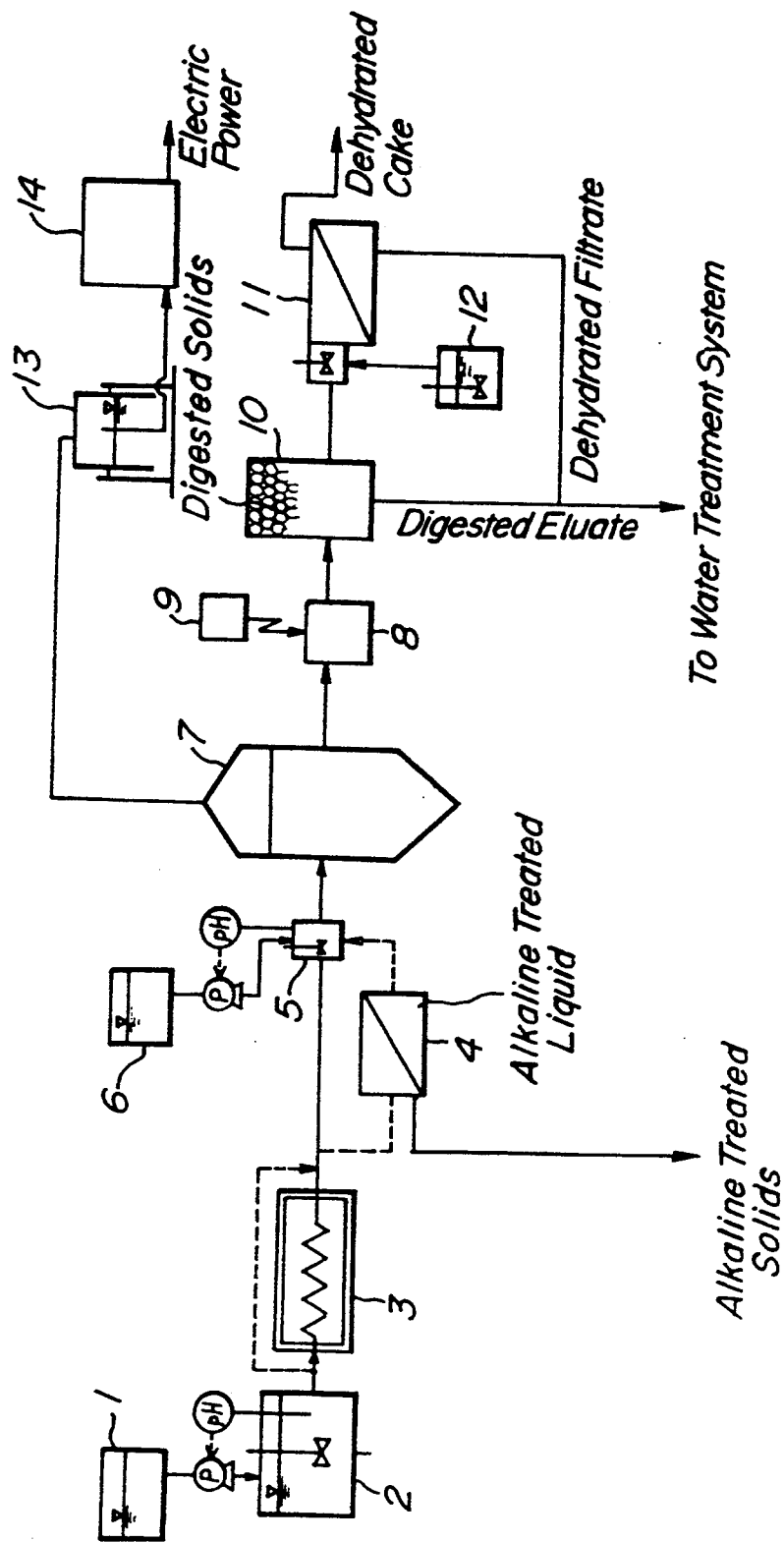
FIG. 1 is a schematic flow sheet of a process used in the practice of the first, second, third and fourth methods of the present invention.

1. . . . alkaline storage tank
2. . . . hot alkaline treating tank
3. . . . tubular type hot alkaline treating tank
4. . . . alkaline treated phase separation apparatus for separating hot alkaline treated sludge
5. . . . pH adjusting tank
6. . . . pH adjutant storage tank 7. . . . anaerobic digestion tank
8. . . . blender tank
9. . . . pH lowering agent storage tank
10. . . . digested solids/digested eluate separation tank for separating digested sludge
11. . . . dehydrater
12. . . . flocculant storage tank
13. . . . gas holder
14. . . . electric power generator
15. . . . $PO_4^{3-}$ storage tank
16. . . . $NH_4^+$ storage tank
17 . . . $Mg^{2+}$ storage tank
18 . . . Struvite separation tank
C . . . automatic concentration meter
F . . . flow meter
pH . . . pH meter
P . . . pump

DETAILED EXPLANATION OF THE INVENTION

Hereinafter, the present invention will be explained in more detail with reference to drawings.

Figure 2:
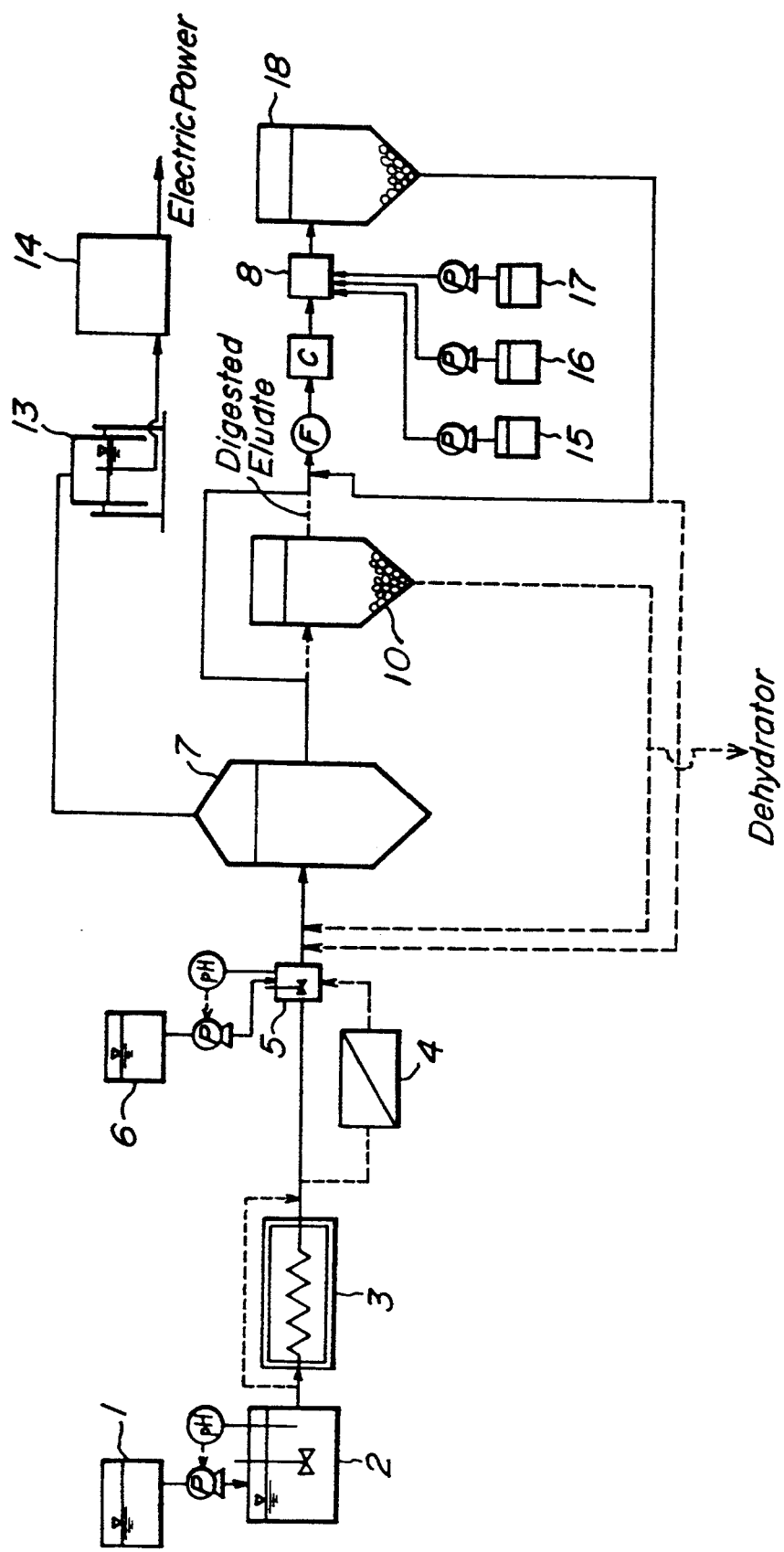
FIG. 2 is a schematic flow sheet of a process used in the practice of the first, second, third and fifth methods of the present invention.

In the processes shown in FIGS. 1 and 2, an organic sludge is at first introduced in a hot alkaline treating tank 2 wherein it is added with alkaline from an alkaline storage tank 1 to control the pH thereof to a value of 7.5-12.5 and heated and solubilized at a temperature of ambient $-100°$ C.

Figure 3:
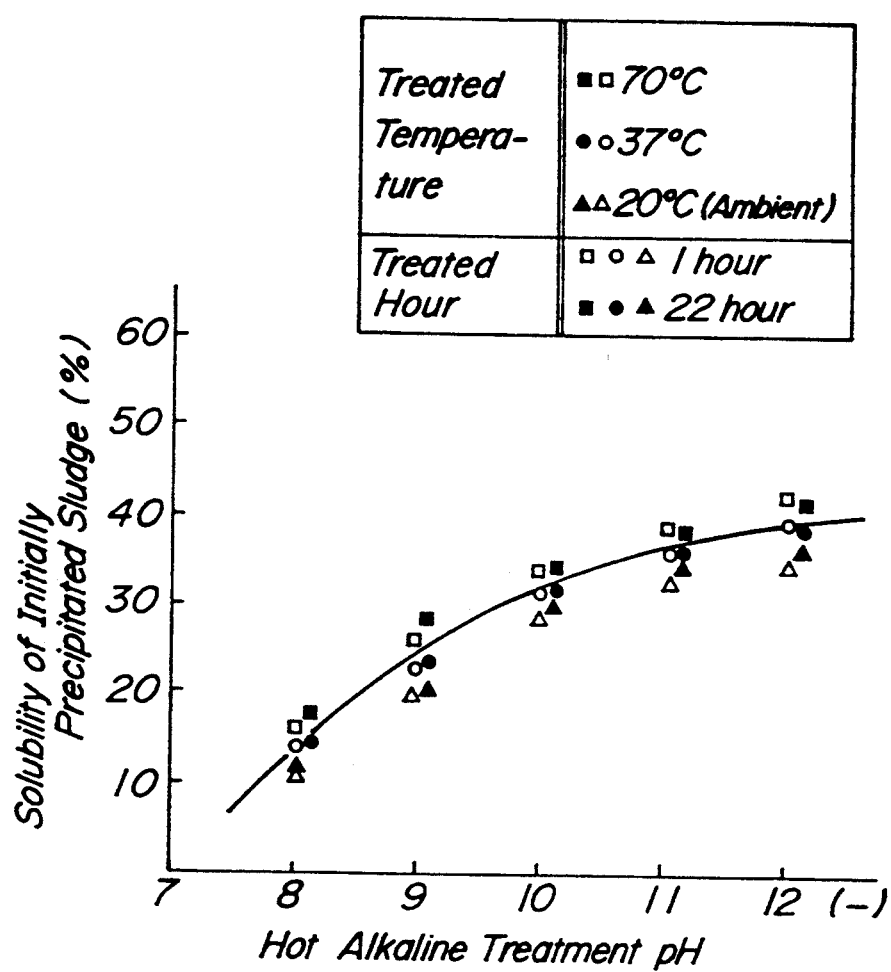
FIG. 3 is a characteristic graph showing a relation between pH of hot alkaline treatment and solubility of initially precipitated sludge taking treating temperature and hour as parameters.
Figure 4:
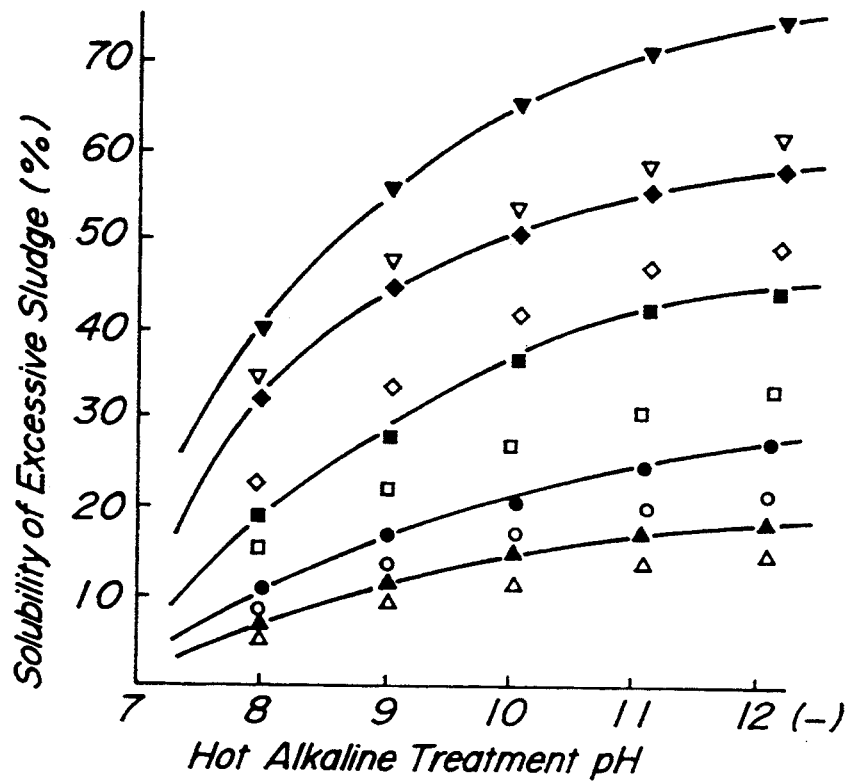
FIG. 4 is a characteristic graph showing a relation between pH of hot alkaline treatment and solubility of excessive sludge taking treating temperature and hour as parameters.

Conditions for the hot alkaline treatment used at the hot alkaline treating tank 2 are determined depending on types of the organic sludge to be treated so as to decrease the cost of heating the sludge and the cost of alkaline to be added and so as to form soluble organic substances, such as organic acids like acetic acid, etc., which can effectively be used in the later anaerobic digestion treatment. For instance, when the organic sludge to be treated is an initially precipitated sludge, solubility is not so largely dependent on treating temperature as shown in FIG. 3, so that pH is desirably set to a high value of not less than 7.5 for ambient temperature. When the organic sludge to be treated is an excessive sludge, solubility is largely dependent on treating temperature and treating pH as shown in FIG. 4, so that pH is desirably set to a high value of not less than 7.5 and the treating temperature is desirably set to a temperature as high as possible but not exceeding 100° C.

The sludge treated with hot alkaline in this way is then fed as it is, or after once subjected to solid/liquid separation treatment in a solid/liquid separation tank 4 for separating the hot alkaline treated sludge to alkaline treated solids and alkaline treated liquid phase, to a pH adjusting tank 5 wherein it is adjusted to a pH value of 7.3-9.2 by adding alkaline or acid from a pH adjutant storage tank 6, and then to an anaerobic digestion tank 7 together with a return sludge. The hot alkaline treated sludge or the alkaline treated liquid of the hot alkaline treated sludge is mixed with the return sludge in the anaerobic digestion tank 7. The operation of adjusting pH in the anaerobic digestion tank 7 is not necessary and may be dispensed with, if the contents fed in the anaerobic digestion tank 7 has already a pH value of 7.3-9.2 before adding alkaline or acid from a pH adjutant storage tank 6.

In the anaerobic digestion tank 7, anaerobic digestion is effected at an alkaline condition of a pH of 7.3-9.2 and a digestion temperature of 20°-60° C., and generated digestion gas containing methane is stored in a gas holder 13 and the resultant digested sludge is fed to a blender tank (precipitation tank) 8 from the anaerobic digestion tank 7. In case when the organic sludge is an easily soluble or decomposable sludge which can expect solubilization thereof in the process of the anaerobic digestion treatment without using the hot alkaline treatment, naturally the hot alkaline treating tank 2 may be omitted and the anaerobic digestion treatment may be performed in the anaerobic digestion tank 7 at the pH of 7.3-9.2.

In the anaerobic digestion tank 7, the sludge is digested at an alkaline condition of a pH of 7.3-9.2, so that carbon dioxide dissolved in the sludge can be dissociated into $HCO_3^-$ ions and $CO_3^{2-}$ ions, and total sum of $CO_2$, $HCO_3^-$ and $CO_3^{2-}$ concentrations can be maintained high as compared with a case when the sludge is digested at neutral condition. Generally, methane gas-forming reaction performed by methane-forming bacteria is expressed by the following formulae of (1) and (2).

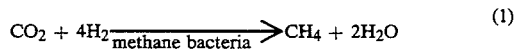  (1)

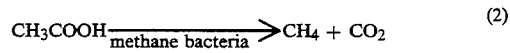  (2)

  (3)

Therefore, in the present invention, carbon dioxide dissolved in an organic sludge is reduced to methane gas through the reaction course (1) in addition to the reaction course (2). It is heretofore said that accumulation of propionic acid prevents methane fermentation in the anaerobic digestion treatment and that such prevention is caused by obstruction of the activity of bacteria, such as, Syntrophbactar and the like which decomposes propionic acid, due to $H_2$ formed in the reaction course (3). However, in the present invention $CO_2$ is dissolved in a large amount in the sludge in the reaction course (1), so that the amount of $H_2$ existing in the reaction (1) is deficient and is a rate-determining factor of the reaction course (1). Hence, $H_2$ is not a cause of obstruction of the activity of the propionic acid-decomposing bacteria in the reaction course (3), so that an organic sludge can advantageously be treated without accumulation of propionic acid.

Methane-forming bacteria which utilize $H_2$ and $CO_2$ as resources can be propagated without issuing out from the digestion tank even when the length of the digestion tank is short, so that the capacity of the digestion tank can be made small. In this way, with the increase of methane content in the digestion gas generated in the anaerobic digestion tank 4, the amount of methane generated by digestion in the anaerobic digestion tank 7 is increased relative to decreased amount of the organic sludge due to the anaerobic digestion. Therefore, the capacity of the anaerobic digestion tank can be made small due to reduction of the digestion time according to the present invention.

Moreover, two merits are obtained that generation of electric power in fuel cells and the like using the gas can be efficiently performed by the increase of methane content in the digestion gas, and that the amount of the recovered methane can be increased even when an anaerobic digestion treatment of about the same extent of digestion ratio is performed by virtue of increased amount of generated methane relative to decreased amount of the organic sludge. Furthermore, a merit is obtained that $H_2S$ gas which is a cause of problem when providing the digestion gas to a fuel cell or the like is formed in a small amount resulting in a small content in the generated digestion gas because the digestion of the sludge is effected at an alkaline condition. Methane content in the digestion gas and generated methane gas amount relative to decreased amount of the organic sludge when an excessive sludge is treated by the alkaline treatment and then anaerobically digestion treated at respective pH according to the present invention, are respectively shown in FIGS. 5 and 6.

Figure 5:
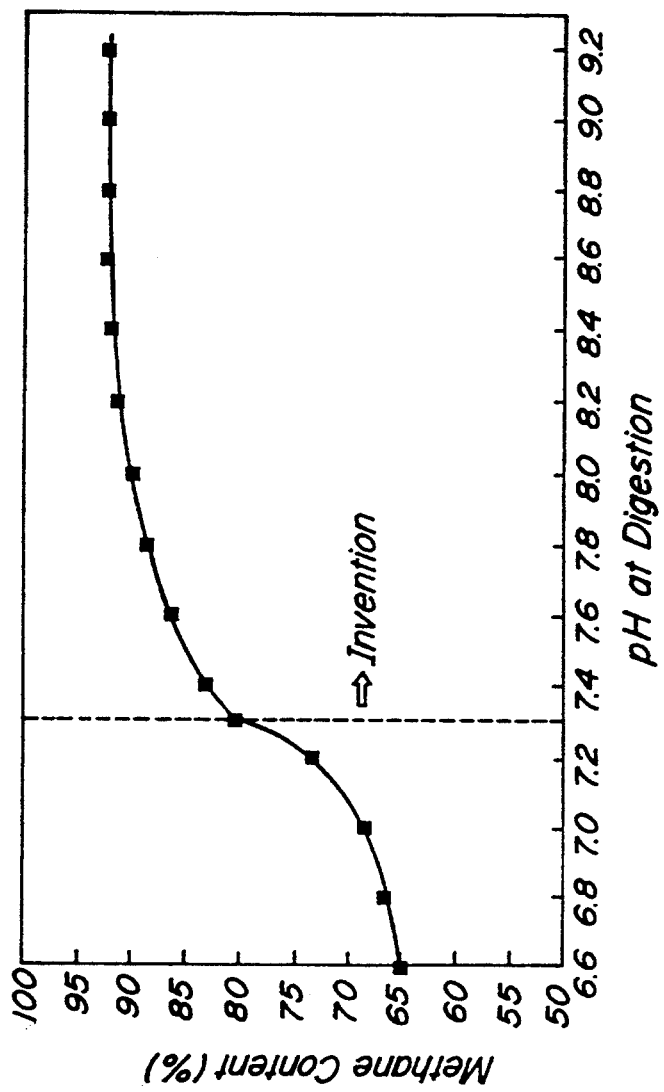
FIG. 5 is a characteristic graph showing a relation between pH at digestion and methane content.
Figure 6:
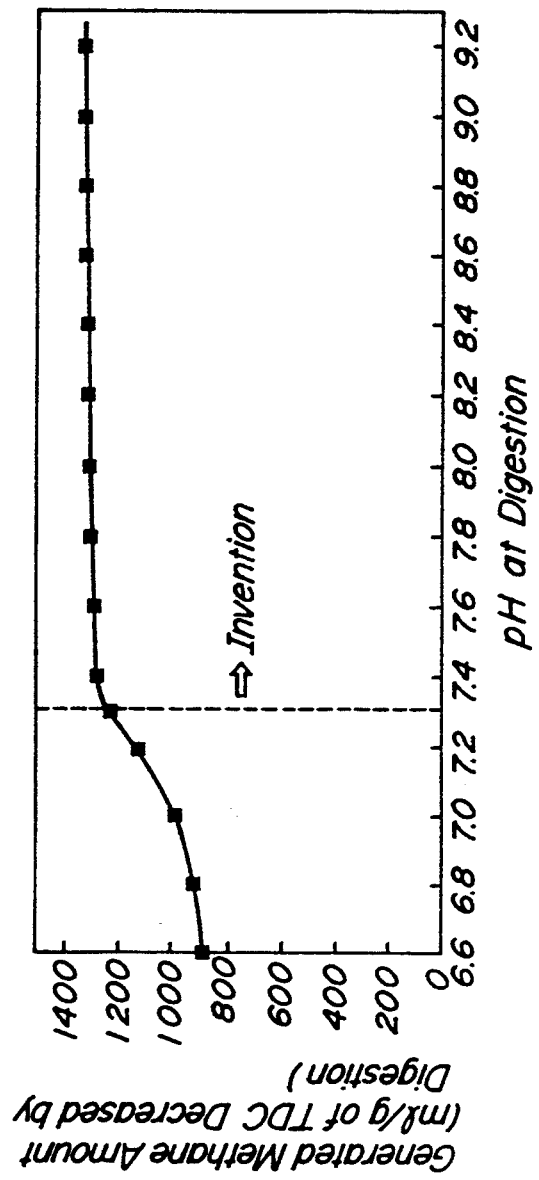
FIG. 6 is a characteristic graph showing a relation between pH at digestion and amount of generated methane.
Figure 7:
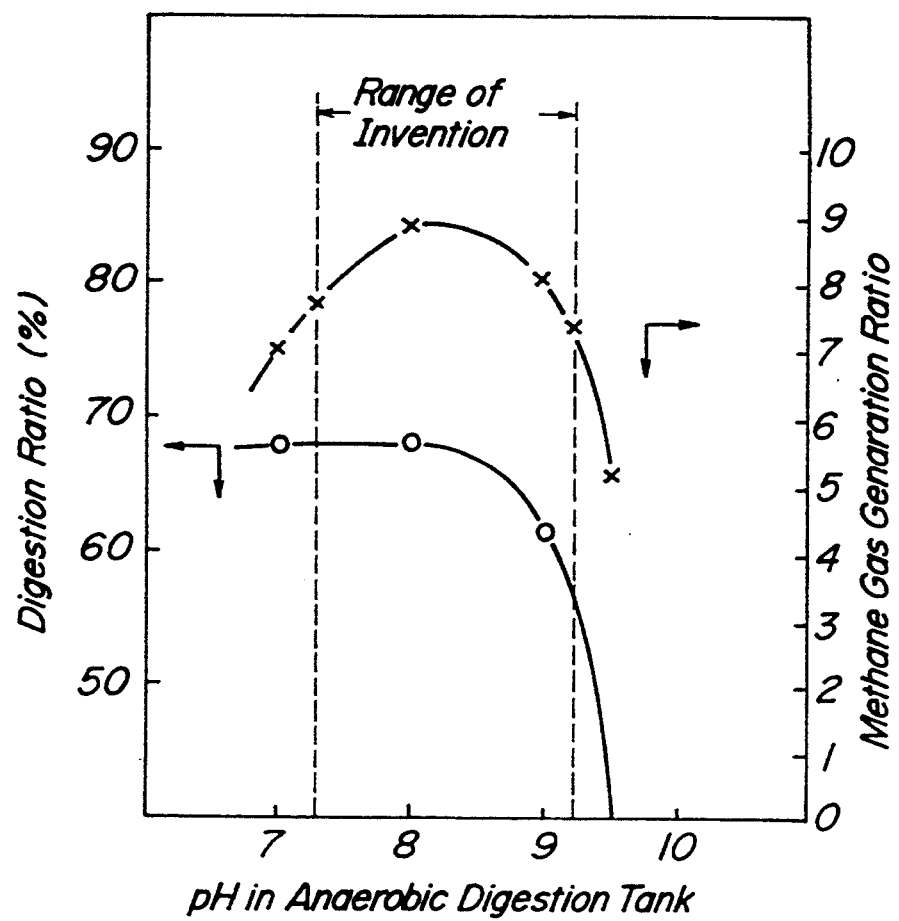
FIG. 7 is a characteristic graph showing a relation between pH in an anaerobic digestion tank and digestion ratio and a relation between pH in an anaerobic digestion tank and ratio of generated methane gas.
Figure 8:
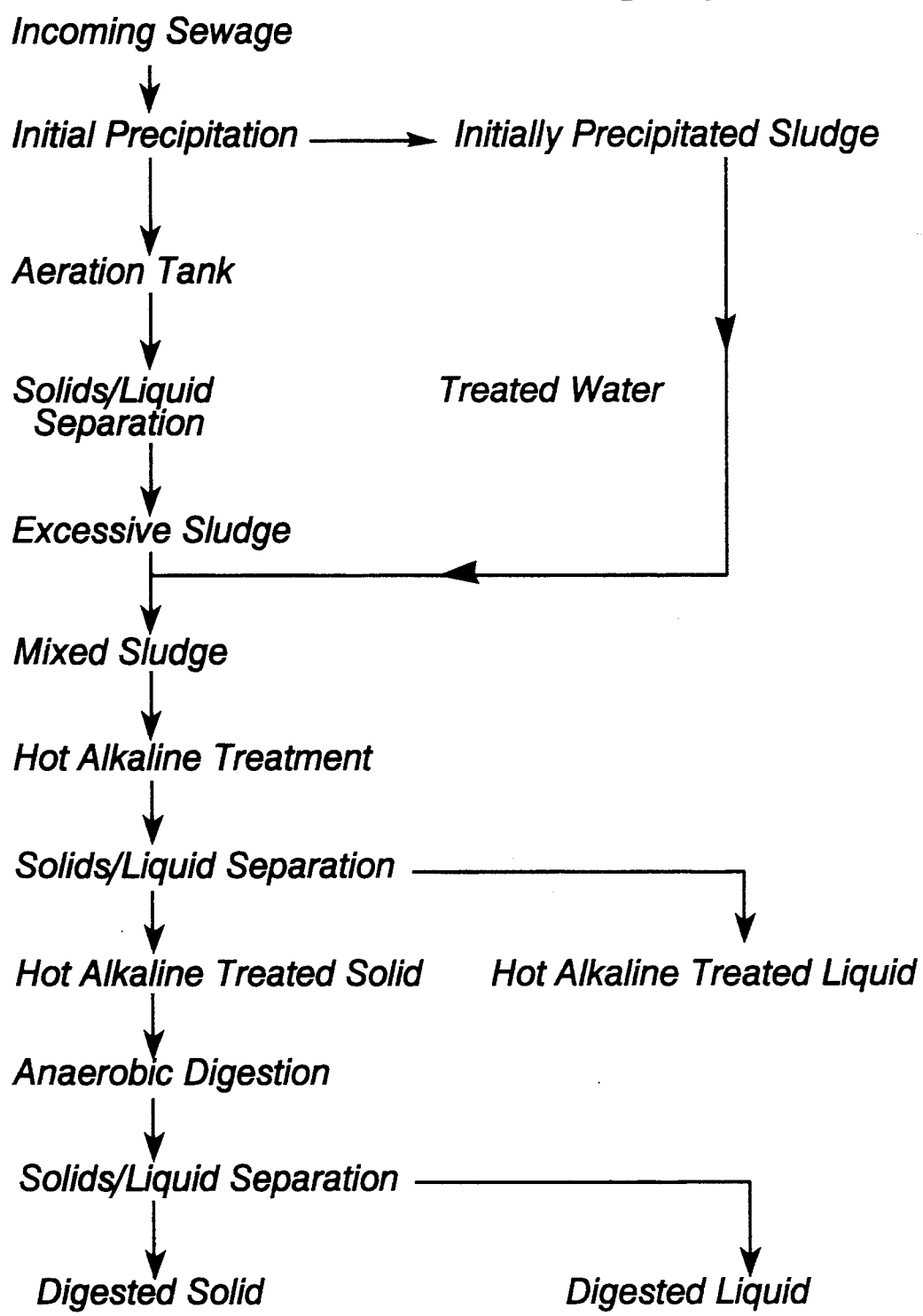
FIG. 8 is a flow sheet of the methods of the present invention.

As shown in FIGS. 5 and 6, when the pH is 7.3 or more than 7.3, methane content and methane gas generation ratio can be maintained high. However, when the digestion pH exceeds 9.2, digestion ratio is considerably decreased, so that methane gas generation ratio is decreased.

When the hot alkaline treating tank 2 of FIGS. 1 and 2 is used as an alkaline mixing tank and a tubular type hot alkaline treating tank 3 is used, an organic sludge is added and mixed with alkaline in the hot alkaline treating tank 2 and then passed to the tubular hot alkaline treating tank 3 while heated to a temperature in a range of ambient to 100° C. to solubilize organic matters in the organic sludge. If higher temperature is used in this range of not exceeding 100° C., viscosity of the sludge is decreased and the solubility of the sludge is increased. If a higher temperature exceeding 100° C. over this range is used, structural problems of the treating apparatus arise, through the pressure of the sludge becomes not less than 1 atm. In this case, when the concentration of the organic sludge is high, a double tubular type heat exchanger is usually used as the tubular type hot alkaline treating tank 3. However, a plate type heat exchanger or the like having a high heating efficiency is preferably used as the hot alkaline treating tank 3 if it is available. If the tubular type hot alkaline treating tank etc., is used solely for the heat treatment without addition of alkaline, methane fermentation reaction and the like anaerobic digestion reaction start in the hot alkaline treating tank 3 to generate a large amount of $CH_4$ and $CO_2$ gases, so that capacitical volume of the hot alkaline treating tank 3 that can practically be used is substantially decreased, and if the plate type heat exchanger is used solely for the heat treatment without addition of alkaline, gas is clogged in the heat exchanger to increase a dead space therein, so that a sufficient effect of the treatment cannot be achieved. In the present invention, there is no generation of $CH_4$ gas in the alkaline treatment step because methane fermentation bacteria is not living in the alkaline treatment step, and $CO_2$ gas if generated is substantially dissolved in the sludge because the sludge is treated in an alkaline condition. However, if the temperature of the step exceeds 70° C., $CO_2$ gas is dissolved in the sludge in only a small amount, so that the volume of the generated $CO_2$ gases cannot be neglected, and hence in such a case the temperature of the step should be cared not to exceed 70° C.

In this process, pH of the organic sludge at the outlet of the tubular type hot alkaline treating tank 3 becomes lower than that at the hot alkaline treating tank 2, and extent of the lowering of pH varies depending on residence time, types and concentration of the organic sludge, so that alkaline is charged in the hot alkaline treating tank 2 so as to obtain a desired alkaline condition at the outlet of the tubular type hot alkaline treating tank 3. By using the tubular type treating tank in this way, an organic sludge can be uniformly treated with a uniform treating time to improve solubility thereof.

If an organic sludge is considerably solubilized by the hot alkaline treatment to increase the concentration of soluble organic matters in the organic sludge, an anaerobic digestion tank 7 containing a bacteria-fixing carrier packed therein is preferably used. In order to accelerate an anaerobic digestion of an organic sludge, anaerobic bacteria has to be held at a high concentration in the digestion treatment, and the use of a carrier realizes fixation and accumulation of the anaerobic bacteria thereon. By this arrangement, the organic sludge solubilized by the hot alkaline treatment can be anaerobically treated highly efficiently with a high concentration of an anaerobic bacteria.

In case when the alkaline treated liquid phase obtained by the separation of alkaline treated solids/alkaline treated liquid of an organic sludge after the hot hot alkaline treatment is supplied to the anaerobic digestion tank 7 containing a bacteria-fixing carrier packed therein, an efficient anaerobic digestion treatment can be achieved in a short treating time.

In the process shown in FIG. 1, the hot alkaline treated organic sludge is digested in the anaerobic digestion tank 7 and added with a pH adjutant, such as, acid or alkali from a storage tank 6 and then introduced in the blender tank 8 wherein it is added with a pH lowering agent from a storage tank 9. As a result, the carbonate ions, bicarbonate ions and carbon dioxide dissolved in the digested sludge are changed to carbon dioxide gas, so that a mixture of the digested sludge and the carbon dioxide gas is charged in a digested solids/digested eluate phase separation tank 10 for separation of the digested solids from the digested eluate. An amount of generated carbon dioxide gas is theoretically 7333 mg/l when the pH of the digested sludge is decreased to 7 from 8.

In the digested solids/digested eluate separation tank 10, the formed carbon dioxide gas is adhered to the solid components in the digested sludge to decrease apparent specific gravity of the solid components thereby to float the solid components. If the blending in the blender tank 8 is complete, the floating of the solid components in the digested solids/digested eluate separation tank 10 is usually completed within about 30–60 minutes to separate a digested solids having a twice more large concentration than the digested sludge from a purified digested eluate. The digested solids are added with a flocculant from a flocculant storage tank 12 and then separated in a dehydrater 11, while the purified digested eluate is flowed to a subsequent water treatment system not shown.

In the process shown in FIG. 2, the hot alkaline treated organic sludge is anaerobically digested at a temperature of 20°–60° C. in the anaerobic digestion tank 7 supplied with a pH adjutant, such as, acid or alkaline from a storage tank 6 and then introduced in the blender 8 through a flow meter F and an automatic concentration meter C via an optional solids/liquid separation tank 10. A digested gas containing methane obtained from the anaerobic digestion tank 7 is subsequently stored in the gas holder 13 and fed to an electric power generating plant 14 to generate electric power. A digested sludge obtained from the anaerobic digestion tank 7 is subsequently fed to the blender 8 and added with $PO_4^{3-}$, $NH_4^+$ and $Mg^{2+}$ from respective sources 15, 16 and 17. The flow meter F measures flow rate of the digested sludge and the automatic concentration meter C automatically measures pH and concentrations of $Mg^{2+}$, $NH_4^+$ -N and $PO_4^{3-}$ -P. Naturally, an easily soluble organic sludge not having a necessity of the hot alkaline treatment may be treated with an alkaline treatment without heating, or the hot alkaline treatment tank 2 can be dispensed with to perform the anaerobic digestion treatment in the anaerobic digestion tank 7 at a pH of 7.3–9.2.

A reason why the pH in the anaerobic digestion tank 7 is maintained at the range of 7.3–9.2 is because, if the pH is lower than 7.3, an organic sludge cannot sufficiently be solubilized and ammonium salt of magnesium phosphate cannot be crystallized in the later described process as described later, and if the pH exceeds 9.2, the anaerobic digestion is obstructed.

Depending on measured concentrations of $Mg^{2+}$, $NH_4^+$-N and $PO_4^{3-}$ -P, at least one or two of $Mg^{2+}$, $NH_4^+$ and $PO_4^{3-}$ is added to the digested sludge in the blender 8. In the present invention, ammonium salt of magnesium phosphate expressed by Struvite is crystallized to remove phosphorus and nitrogen. Therefore, when phosphorus ($PO_4^{3-}$ -P) is desired to remove, $Mg^{2+}$ and/or $NH_4^+$ deficient for crystallization of Struvite is added to the digested sludge depending on necessity. These addition is effected from the storage tanks 15, 16 and 17 as described above.

Struvite is a crystal of $MgNH_4PO_4 \cdot 6H_2O$ wherein the molecular ratio of magnesium, nitrogen and phosphorus is 1:1:1. Therefore, if at least one of $Mg^{2+}$, $NH_4^+$ and $PO_4^{3-}$ deficient to satisfy the molecular ratio is added to the digested sludge, crystals of Struvite are formed in the blender 8 according to the following reaction:

$$Mg^{2+} + NH_4^+ + HPO_4^{2-} + OH^- + 6H_2O$$
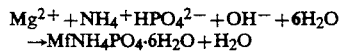
$$\rightarrow MfNH_4PO_4 \cdot 6H_2O + H_2O$$

The Struvite has a property that its solubility is rapidly decreased in alkaline region to precipitate as crystals. However, in the present invention, pH in the anaerobic digestion tank 7 is maintained at a pH of 7.3–9.2 and pH in the blender 8 is maintained also at a pH of 7.3–9.2, so that crystals of Struvite are efficiently formed without addition of an alkaline.

In this way, a liquid containing crystals of Struvite, etc., made of ammonium magnesium phosphate hexahydrate is separated from solids in a Struvite separation tank 18 to obtain a digested eluate and a concentrated digested sludge containing crystals of ammonium magnesium phosphate hexahydrate. The portion of the concentrated digested sludge containing crystals of ammonium magnesium phosphate hexahydrate is returned to the anaerobic digestion tank 7 as a return sludge and a portion of the concentrated digested sludge is returned to the blender tank 8 as a seed crystal for accelerating the crystallization of the ammonium magnesium phosphate hexahydrate. As a result, concentrations of phosphorus and nitrogen contained in the digested eluate can widely be decreased to mitigate the load of the subsequent water treatment system. The ammonium magnesium phosphate hexahydrate which is useful as a fertilizer and the like can advantageously be recovered in a separated state from the sludge.

Figure 9:
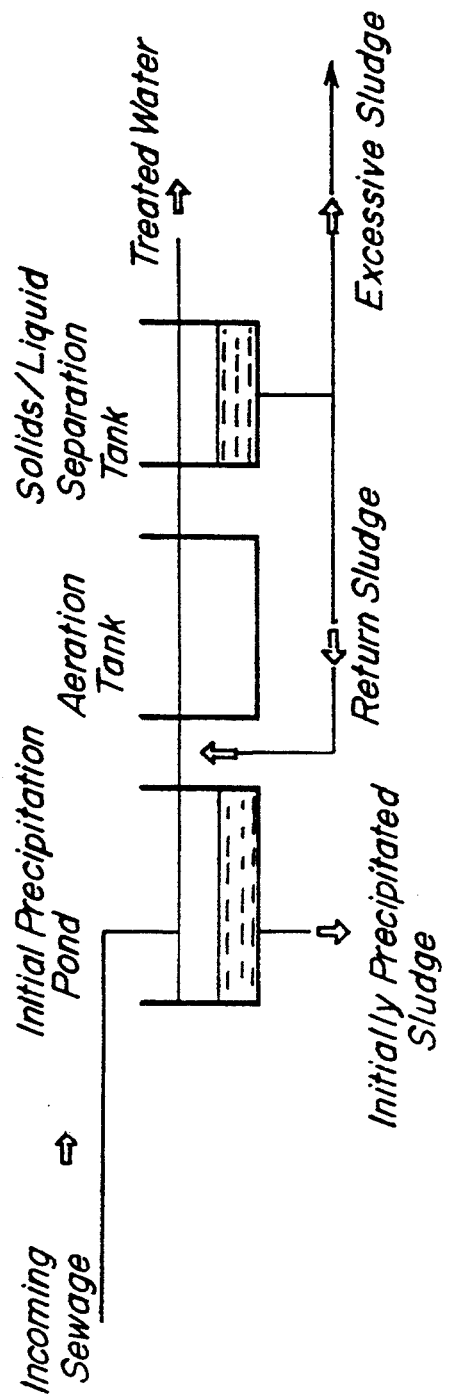
FIGS. 9 and 10 are flow diagrams of the sixth method of the present invention.

In the sixth method of the present invention, the initially precipitated sludge obtained by the solids/liquid precipitation treatment in the initial precipitation pond contains a large quantity of sand or the like inorganic matters, so that it is easily treated, whereas the excessive sludge obtained by the solids/liquid separation treatment in a solids/liquid separation apparatus of the aerated initially separated liquid contains a large quantity of organic matters, so that it is difficult to treat. In this method, a portion of the excessive sludge is returned as a seed sludge (return sludge) to the aeration apparatus. Such feature of the sixth method of the present invention is shown in flow diagrams of FIGS. 9 and 10. By this arrangement, both the excessive sludge and the initially precipitated sludge are treated at respectively most appropriate conditions. Preferably, the hot alkaline treatments of the initially precipitated sludge and the excessive sludge are effected respectively at a pH range of 7.5–10.5 in about a one hour and 7.5–12.5 in about 22 hrs. as seen from FIGS. 3 and 4 from the view points of solubility and cost of addition of an acid.

DESCRIPTION OF THE PREFERRED EMBODIMENTS

Hereinafter, the present invention will be explained in more detail with reference to examples. Examples 1–4 and Comparative Examples 1–2

The present invention was put into practice under the conditions as shown in the following Table 1.

In these examples, an excessive sludge was used as an organic sludge, and experiments were conducted on effect of the non-adjustment of pH in the later stage of solubilization caused by hot alkaline treatment using different pH on the anaerobic digestion (Examples 1–3), effect of the treatment of a hot alkaline treated organic sludge in an anaerobic digestion tank 7 containing a packed carrier (Example 4), and effect of anaerobic digestion caused by hot alkaline treatment of a sludge treated with conventional anaerobic digestion at a neutral pH after adjustment (Comparative Examples 1–2). The results are shown in Table 2.

TABLE 1

| | Conditions for Experiment | Comparative Example 1 | Comparative Example 2 | Examples 1 | Examples 2 | Examples 3 | Examples 4 |
|---|---|---|---|---|---|---|---|
| | Classification of Technique | Conventional | | Invention | | | |
| Organic Sludge | Concentration of Initial Excess Sludge (mg/l) | | | 31500 | | | |
| | Concentration of Organic Matters in Initial Excess Sludge (mg/l) | | | 27100 | | | |
| Solubilization | Treating Method | Hot Alkaline Treatment under Controlled Constant pH | | | | | |
| | Temperature (°C.) | | | 70 | | | |
| | pH (—) | 8.0 | 9.8 | 8.0 | 8.8 | 9.8 | 8.8 |
| | Alkaline Extent of Sludge (mg $CaCO_3$/l) | 2400 | 4800 | 2400 | 3200 | 4800 | 3200 |
| | Time (Hr) | 6 | 6 | 6 | 6 | 6 | 6 |
| Anaerobic | Treating Method | Completely Mixed Reaction | | | | | Carier |

TABLE 1-continued

| Conditions for Experiment | Comparative Example 1 | Comparative Example 2 | Examples 1 | Examples 2 | Examples 3 | Examples 4 |
|---|---|---|---|---|---|---|
| Digestion | | | | | | |
| Temperature (°C.) | | | | 37° C. | | Packed |
| pH (—) | Adjusted 7.0 | Adjusted 7.0 | Non-Adjusted 7.3 | Non-Adjusted 8.2 | Non-Adjusted 9.2 | Non-Adjusted 8.2 |
| Load of Organic Matter (kg Organic Matter/m³ · day) | 4.3 | 4.3 | 4.3 | 4.3 | 4.3 | 4.3 |
| Time (Day) | | | 6.4 | | | 3.8 |

Note:
Examples 1–3 correspond to the first method of the present invention and the flow sheet of FIG. 1.
Example 4 corresponds to the fourth method of the present invention and the flow sheet of FIG. 2.

TABLE 2

| | Conditions for Experiment | Comparative Example 1 | Comparative Example 2 | Example 1 | Example 2 | Example 3 | Example 4 |
|---|---|---|---|---|---|---|---|
| | Classification of Technique | Conventional | | Invention | | | |
| Organic Sludge | Concentration of Initial Excess Sludge (mg/l) | | | 31500 | | | |
| | Concentration of Organic Matters in Initial Excess Sludge (mg/l) | | | 27100 (100–12700) | | | |
| | Concentration of Soluble Organic Matters in Initial Excess Sludge (mg/l) | | | 1000 | | | |
| Solubilization | Solubility (%) | 52.1 | 69.5 | 52.1 | 60.3 | 69.5 | 60.3 |
| | Soluble Orgainic Matters (mg/l) | 14600 | 19100 | 14600 | 16700 | 19100 | 16700 |
| | Amount of Formed Soluble Organic Matters (mg/l) | 13600 | 18100 | 13600 | 15700 | 18100 | 15700 |
| | Amount of Formed Organic Acid (mg/l) | 2800 | 4100 | 2300 | 3500 | 4100 | 3500 |
| | Amount of Formed Acetic Acid (mg/l) | 1800 | 3000 | 1800 | 2600 | 3000 | 2600 |
| Anaerobic digestion | Digestion pH | 7.0 | 7.0 | 7.3 | 7.8 | 9.2 | 7.8 |
| | Digestion Ratio (Decrease Ratio of Organic Matters) (%) | 66.2 | 68.0 | 68.0 | 68.0 | 65.0 | 75.0 |
| | Methane Gas Generation Ratio (m³ gas/m³ organic sludge) | 7.5 | 7.7 | 10.1 | 11.35 | 11.0 | 12.70 |
| | Amount of Generated Methane Gas (l gas/l decreased amount of TOO) | 0.90 | 0.90 | 1.18 | 1.32 | 1.34 | 1.32 |
| Gas composition | Hydrogen Sulfide (%) | 0.1 | 0.1 | 0 | 0 | 0 | 0 |
| | Methane (%) | 72.0 | 71.5 | 80.5 | 88.5 | 92.1 | 88.5 |
| | Carbon Dioxide (%) | 27.9 | 28.4 | 19.5 | 11.5 | 7.9 | 11.5 |
| Result of Dehydration of Precipitated Sludge | CST of Sludge added with a Flocculent (sec) | 13.8 | 14.5 | 13.7 | 12.6 | 12.3 | 12.9 |
| | Water Content in Cake (%) | 73.5 | 73.5 | 73.0 | 74.5 | 73.5 | 72.9 |
| | Organic Matters Content in Cake (%) | 72.5 | 72.3 | 73.6 | 71.5 | 72.6 | 70.9 |
| Digested Eluate | Concentration of Organic Matters (mg/l) | 2080 | 2100 | 2160 | 2230 | 2450 | 1830 |
| | BOO Concentration (mg/l) | 1550 | 1570 | 1610 | 1720 | 1800 | 930 |

As shown in Table 2, in the conventional cases of a hot alkaline treatment plus pH adjusted anaerobic digestion treatment (pH=7), a generated gas was obtained containing 71–72% of methane and a small amount of hydrogen sulfide, and a methane gas generation ratio was 7–8, whereas in the present invention, though the digestion ratio was substantially the same, methane generation ratio relative to decreased amount of organic sludge caused by digestion was increased and a generated gas was obtained containing 80% or more of methane and no hydrogen sulfide detected and a methane gas generation ratio was at least 10 and predominance was observed from a viewpoint of gas generation. Also, by packing a carrier in the anaerobic digestion tank 7, improvement in the digestion ratio and purification of the digested eluate were observed. The digestion gas having a large content of methane and no hydrogen sulfide is very advantageous in generation of electric power in fuel cells and the like.

EXAMPLE 5

The digested solids obtained by the present invention (FIG. 1) were added with a small amount of flocculant and subjected to filtration on a filter press dehydrater or a belt press dehydrater in a process as shown in FIG. 1. The results are shown in the following Tables 3 and 4.

TABLE 3

| Sludge | Addition Ratio of Flocculant | De-hydrator | Ability of Dehydration | Water Content in Cake |
|---|---|---|---|---|
| Usual Digested Sludge | Salt Iron 20%/TS Lime 70%/TS | Filter Press | 1.2 kg DS/ m² hr | 54% |
| Concentrated Disgested Sludge of Invention | Salt Iron 0%/TS Lime 50%/TS | | 1.8 kg DS/ m² hr | 50% |

TABLE 4

| Sludge | Addition Ratio of High Molecular Flocculant | De-hydrator | Ability of Dehydration | Water Content in Cake |
|---|---|---|---|---|
| Usual Digested Sludge | 1%/TS | Belt Press | 70–100 kg DS/ m² hr | 80% |
| Concentrated Digested Sludge of Invention | 0.67%/TS | | 200 kg DS/ m² hr | 76% |

Note:
Speed of filter cloth was 1 m/s and belt tension pressure was 3 kg/cm²

As seen from Tables 3 and 4, the digestion solids (which are the concentrated digested sludge) obtained by the present invention can be treated on either of a filter press dehydrater or a belt press dehydrater with highly improved dehydration efficiencies, largely decreased water content in the dehydrated cake and largely improved strippability of the cake from the filter cloth of the dehydrater.

EXAMPLES 6-7 AND COMPARATIVE EXAMPLE 3

The present invention was performed in order to decrease phosphorus content in the digested eluate in a process as shown in FIG. 2. The results are shown in the following Table 5.

be improved with increase of pH beyond this range, an obstruction is formed in the anaerobic digestion and the digestion is not performed well.

EXAMPLE 8 AND COMPARATIVE EXAMPLE 4

An example of the sixth method of the present invention will be explained herein in comparison with a conventional example.

Figure 10:
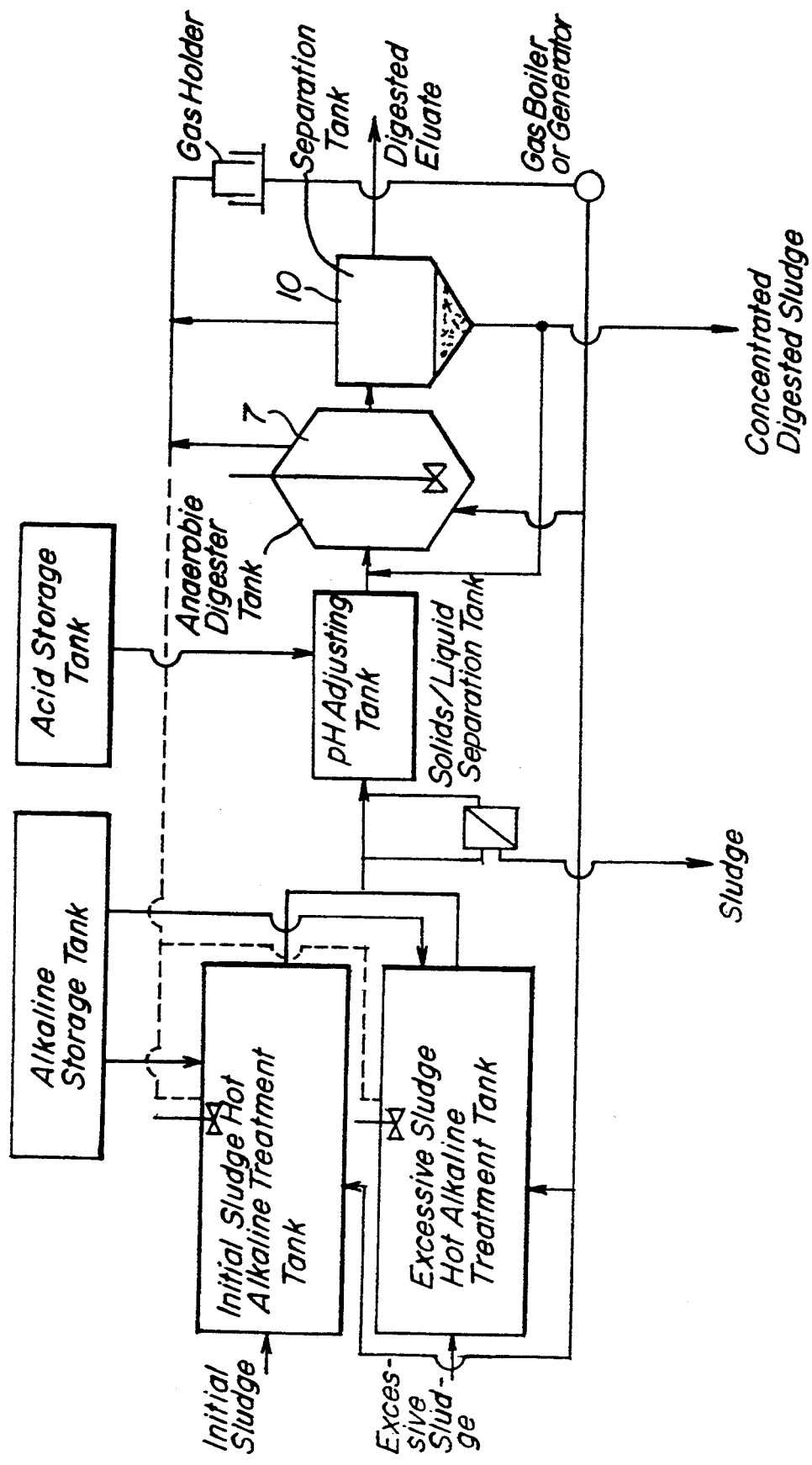

The sixth method of the present invention was carried out into effect using the process as shown in FIG. 10 and the conditions as described in the following Table 6.

The condition for hot alkaline treatment for solubilizing mixed raw sludges in the conventional example was 70° C., 22 hrs. and pH 9.0. In the present invention, the

TABLE 5

|  | Sample | | | | | | | | |
|---|---|---|---|---|---|---|---|---|---|
|  | Comparative Example 3 (pH = 6.8) | | | Example 5 (pH = 7.4) | | | Example 6 (pH = 9.2) | | |
| Substance | Mg | N | P | Mg | N | P | Mg | N | P |
| Initial Concentration (mg/L) | — | 765 | 126 | — | 1280 | 175 | — | 1310 | 202 |
| Concentration after Addition (mg/L) | 98 | 0 | 0 | 137 | 0 | 0 | 158 | 0 | 0 |
| Crystallization (%) | 63.8 | | | 89.6 | | | 96.6 | | |
| Concentration of P in Digested Elute | 49.0 mg/L | | | 19.6 mg/L | | | 10.9 mg/L | | |
| Removal Ratio of P | 61.1% | | | 88.8% | | | 94.6% | | |

As seen from Table 5, in Examples 6 and 7 treated with a pH of 7.3-9.2 within the range of the present invention high crystallization degrees of Struvite were obtained and Example 6 could remove 88.9% of phosphorus and Example 7 could remove 94.6% of phosphorus. However, in Comparative Example 3 crystallization degree of Struvite was low and 61.1% of phosphorus was merely removed. Though crystallization degree of Struvite and removal ratio of phosphorus may excessive sludge was hot alkaline treated in the same condition as described above, however, the initially precipitated sludge was hot alkaline treated at a condition of 37° C., 1 hr. and pH 9.0, because the initially precipitated sludge is not significantly effected by differences in temperature and treating time, as shown in FIG. 4. The results are shown also in the following Table 6.

TABLE 6

|  | Item | Comparative Example 4 | Example 8 | |
|---|---|---|---|---|
| Hot alkaline treatment | Sludge | Mixed sludge | Excessive sludge | Initially precipitated sludge |
|  | Solubility (%, decrease % of VSS) | 38% | 47% | 30% |
|  | Concentration of organic acid after the treatment (mg/L) | 1750 | 2760 | 1410 |
|  | Concentration of organic acid before the treatment (mg/L) | 810 | 670 | 880 |
|  | Addition ratio of alkaline (NaOH) (%/TS) | 12 | 12 | 5 |
| Anaerobic digestion treatment | Digestion ratio (%, VSS decrease ratio) | 55 | 62 | |
|  | Generated methane gas ratio ($CH_4$ m$^3$/sludge m$^3$) | 10.3 | 11.8 | |
|  | Methane gas ratio (%) | 89 | 89 | |
|  | Generated amount of methane gas (m$^3$/charged kg VS) | 413 | 471 | |

TABLE 6-continued

| Item | Comparative Example 4 | Example 8 |
|---|---|---|
| (m³/digested kg VS) | 750 | 760 |

As seen from the above Table 6, regarding the solubilization due to the hot alkaline treatment, the Conventional Example 4 has a solubility of 38% which positions at an intermediate between the solubility 47% of the excessive sludge and the solubility of 30% of the initially precipitated sludge. However, the excessive sludge of the Example 8 has a concentration of organic acid of 2760 mg/l in the solubilized components, which indicates that the excessive sludge was treated by 22 hrs. of the hot alkaline treatment to a further solubilized state of acid fermentation in advance to the anaerobic digestion treatment. In contrast, in the Conventional Example 4, the hot alkaline treatment of the mixed raw sludges made of a mixture of the initially precipitated sludge and the excessive sludge gave a concentration of organic acid of only 1750 mg/l even under the same condition of the hot alkaline treatment. Therefore, the method of the present invention which treats the different sludges of different properties with a respective different appropriate condition was ascertained as clearly advantageous over the conventional method. In this way, the present method has an advantageous effect of increasing the concentration of organic acid which can be assimilated by the subsequent anaerobic digestion treatment, which is more advantageous than merely increasing the solubility of VSS. Also, as regard to the amount of added alkaline, though Conventional Example 4 needed 12% (g HaOH/g TS) of TS relative to the TS of the mixed raw sludges, the Example 8 needed only a very small amount of 5% relative to the initially precipitated sludge, so that reduction of the cost can be realized. This is because the treating time of the hot alkaline treatment of the initially precipitated sludge was reduced to a very short time of about 1 hr, though the condition of pH 9.0 was the same with that of the excessive sludge.

Moreover, though the digestion ratio was 55% in the Conventional Example 4, the Example 8 had an improved digestion ratio of 62%, and though the generated methane gas ratio was 10.3 m³/sludge m³ in the Conventional Example 4, the Example 8 had an improved value of 11.8 m³/sludge m³, so that the present method was ascertained as efficient method.

Therefore, by the respective optimum solubilizing treatment of the initially precipitated sludge and the excessive sludge having different properties, an efficient solubilizing treatment of sewage sludge can be achieved with a reduced low cost. As a result, recovery of methane gas and volume reduction of the sludge which are characteristic features of anaerobic digestion can be achieved more efficiently than the conventional method.

As explained in detail in the foregoing explanations, the present invention can achieve various advantages as follows.

1  By performing the hot alkaline treatment, digestion rate can be speeded up and digestion ratio is increased.

2  Generated amount of methane gas relative to organic matters decreased in the hot alkaline treatment and the anaerobic digestion treatment, is increased.

3  Recovery ratio of methane relative to charged organic sludge is increased due to 1 and '.

4  Methane content in the digestion gas is increased due to 2 and methanization of $CO_2$ caused by increased amount of $CO_2$ dissolved in the alkaline sludge.

5  Amount of generated $H_2S$ is small.

6  Amount of acid as a neutralizing agent is widely decreased or eliminated, because necessary pH adjustment to around the neutral point conventionally effected in the anaerobic digestion treatment is dispensed with.

7  Due to charging of a carrier in the anaerobic digestion tank, digestion ratio is increased and concentration of organic matters in the digested eluate is decreased.

Also, according to the present invention various advantages can be achieved as follows.

The digested sludge can be subjected to the digested solids/digested eluate separation treatment in a sufficient amount and at a high rate without necessitating plenty of electric power and a complicated apparatus different from conventional pressurized floating concentration method, because an organic sludge is anaerobically digestion treated in an alkaline condition of a pH of at least 7.3 and the digested sludge is rendered to float and separated by the use of carbon dioxide gas liberated by lowering of pH of the digested sludge. Moreover, dehydration ability in the dehydration process can be improved, because the digested solids are concentrated to decrease the alkaline extent thereof, and concentration of phosphorus of ortho phosphorus state in the digested eluate which is returned to a succeeding water treatment system can be decreased due to the use of ferric chloride as a pH decreasing agent and PAC. etc. as a flocculent.

As an alternative method different from the above method, phosphorus and nitrogen in the digested eluate can be removed with high removal ratio to mitigate the load of a succeeding water treatment system by precipitating Struvite made of ammonium magnesium phosphate hexahydrate as crystals. Though the crystals of Struvite are formed in an alkaline condition, addition of alkaline is not necessary, because the digested sludge is already in an alkaline state due to the alkaline treatment or the hot alkaline treatment. Useful ammonium magnesium phosphate hexahydrate can be recovered in addition to removal of phosphorus and nitrogen in the digested eluate, and may be used as a fertilizer.

Although the present invention has been explained with specific examples and numeral values, it is of course apparent to those skilled in the art that various changes and modifications thereof are possible without departing from the broad spirit and aspect of the present invention as defined in the appended claims.

What is claimed is:

1. A method for treating sewage containing organic sludge, comprising:
subjecting the sewage to a solid/liquid precipitation treatment in an initial precipitation pond to obtain an initially precipitated sludge and an initially separated liquid;

aerating the initially separated liquid in an aeration apparatus;

subjecting the aerated initially separated liquid to a solid/liquid separation treatment in a solid/liquid separation apparatus to obtain an excessive sludge;

subjecting the excessive sludge to an alkaline treatment to cause the excessive sludge to become alkaline with a pH of 8.0–9.8 while maintaining the temperature of the excessive sludge at ambient −100° C. to solubilize organic matter in the sludge; and anaerobically digesting the alkaline treated excessive sludge at a temperature of 20°–60° C. at a pH of 7.8–9.2 to obtain a digested sludge.

2. The method of claim 1, wherein the excessive sludge is mixed with the initially precipitated sludge to form a mixed sludge before the alkaline treatment.

3. The method of claim 2, further comprising the step of generating at least one of electric power and thermal energy using, as a raw material, a digested gas generated during the anaerobic treatment.

4. The method of claim 2, further comprising:
lowering the pH of the anaerobically digested sludge to liberate gaseous carbon dioxide therefrom; and
utilizing the liberated gas to float the digested sludge in digested eluate thereby separating digested solids from the digested eluate, while adding a flocculant to the digested solids for dehydration thereof.

5. The method of claim 2, further comprising:
adding at least one of $Mg^{2+}$, $NH^{4+}$, and $PO_4^{3-}$ to one of the anaerobically digested sludge and a digested eluate obtained by liquid/solid separation of said digested sludge to crystalize ammonium magnesium phosphate hexahydrate;
separating the crystallized ammonium magnesium phosphate hexahydrate from one of the liquid phase of the digested sludge and the digested eluate, respectively, to thereby recover the crystalline ammonium magnesium phosphate hexahydrate and remove at least one of phosphorus and nitrogen from one of the digested sludge and the digested eluate, respectively.

6. The method of claim 1, further comprising the step of generating at least one of electric power and thermal energy using, as a raw material, a digested gas generated during the anaerobic treatment.

7. The method of claim 1, further comprising:
lowering the pH of the anaerobically digested sludge to liberate gaseous carbon dioxide therefrom; and
utilizing the liberated gas to float the digested sludge in digested eluate thereby separating digested solids from the digested eluate, while adding a flocculant to the digested solids for dehydration thereof.

8. The method of claim 1, further comprising:
adding at least one of $Mg^{2+}$, $NH^{4+}$, and $PO_4^{3-}$ to one of the anaerobically digested sludge and a digested eluate obtained by liquid/solid separation of said digested sludge to crystalize ammonium magnesium phosphate hexahydrate;
separating the crystallized ammonium magnesium phosphate hexahydrate from one of the liquid phase of the digested sludge and the digested eluate, respectively, to thereby recover the crystalline ammonium magnesium phosphate hexahydrate and remove at least one of phosphorus and nitrogen from one of the digested sludge and the digested eluate, respectively.

9. A method for treating sewage containing organic sludge, comprising:
subjecting the sewage to a solid/liquid precipitation treatment in an initial precipitation pond to obtain an initially precipitated sludge and an initially separated liquid;
aerating the initially separated liquid in an aeration apparatus;
subjecting the aerated initially separated liquid to a solid/liquid separation treatment in a solid/liquid separation apparatus to obtain an excessive sludge;
subjecting the excessive sludge to an alkaline treatment to cause the excessive sludge to become alkaline with a pH of 8.0–9.8 while maintaining the temperature of the excessive sludge at ambient −100° C. to solubilize organic matter in the sludge;
subjecting the alkaline treated excessive sludge to a solid/liquid separation treatment in a solid/liquid separation apparatus to obtain alkaline treated solids and an alkaline treated liquid; and
anaerobically digesting the alkaline treated liquid at a temperature of 20°–60° C. at a pH of 7.8–9.2 to obtain digested solids.

10. The method of claim 9, wherein the excessive sludge is mixed with the initially precipitated sludge to form a mixed sludge before the alkaline treatment.

11. The method of claim 10, further comprising the step of generating at least one of electric power and thermal energy using, as a raw material, a digested gas generated during the anaerobic treatment.

12. The method of claim 10, further comprising:
lowering the pH of the anaerobically digested solids to liberate gaseous carbon dioxide therefrom; and
utilizing the liberated gas to float the digested solids in digested eluate thereby further separating digested solids from the digested eluate, while adding a flocculant to the digested solids for dehydration thereof.

13. The method of claim 10, further comprising:
adding at least one of $Mg^{2+}$, $NH_4^+$, and $PO_4^{3-}$ to said alkaline treated liquid to crystalize ammonium magnesium phosphate hexahydrate;
separating the crystallized ammonium magnesium phosphate hexahydrate from said alkaline treated liquid to thereby recover the crystalline ammonium magnesium phosphate hexahydrate and remove at least one of phosphorus and nitrogen therefrom.

14. The method of claim 9, further comprising the step of generating at least one of electric power and thermal energy using, as a raw material, a digested gas generated during the anaerobic treatment.

15. The method of claim 9, further comprising:
lowering the pH of the anaerobically digested solids to liberate gaseous carbon dioxide therefrom; and
utilizing the liberated gas to float the digested solids in digested eluate thereby further separating digested solids from the digested eluate, while adding a flocculant to the digested solids for dehydration thereof.

16. The method of claim 9, further comprising:
adding at least one of $Mg^{2+}$, $NH_4^+$, and $PO_4^{3-}$ to said alkaline treated liquid to crystalize ammonium magnesium phosphate hexahydrate;
separating the crystallized ammonium magnesium phosphate hexahydrate from said alkaline treated liquid to thereby recover the crystalline ammonium magnesium phosphate hexahydrate and remove at least one of phosphorus and nitrogen therefrom.

17. A method for treating sewage containing organic sludge by anaerobic digestion, comprising:

subjecting the sewage to a solid/liquid precipitation treatment in an initial precipitation pond to obtain an initially precipitated sludge and an initially separated liquid;

subjecting the initially precipitated sludge to an alkaline treatment at a temperature of ambient to an anaerobical digestion temperature at a pH of 7.5–10.5 to solubilize the initially precipitated sludge;

aerating the initially separated liquid in an aeration apparatus;

subjecting the aerated initially separated liquid to a solid/liquid separation treatment in a solid/liquid separation apparatus to obtain an excessive sludge;

subjecting the excessive sludge to an alkaline treatment at a temperature of 50°–100° C. at a pH of 8.0–9.8 to solubilize the excessive sludge;

mixing the solubilized initially precipitated sludge and the solubilized excessive sludge to obtain a second mixed sludge; and anaerobically digesting the second mixed sludge at a temperature of 20°–60° C. and at a pH of 7.8–9.2.

* * * * *